United States Patent [19]
Coutts et al.

[11] Patent Number: 5,543,422
[45] Date of Patent: Aug. 6, 1996

[54] HETEROCYCLIC AMINES

[75] Inventors: Ian G. C. Coutts, Arnold; Pamela J. Cummins, Clifton, both of England

[73] Assignee: British Technology Group Limited, London, England

[21] Appl. No.: 403,859

[22] PCT Filed: Oct. 1, 1993

[86] PCT No.: PCT/GB93/02048

§ 371 Date: Mar. 23, 1995

§ 102(e) Date: Mar. 23, 1995

[87] PCT Pub. No.: WO94/07875

PCT Pub. Date: Apr. 14, 1994

[30] Foreign Application Priority Data

Oct. 2, 1992 [GB] United Kingdom ............. 9220735

[51] Int. Cl.$^6$ .................. A61K 31/435; A61K 31/395
[52] U.S. Cl. .................. 514/319; 514/315; 514/317; 514/320; 514/324; 514/238.8; 514/422; 514/428; 514/468; 514/443; 544/173; 546/248; 546/202; 548/525; 548/574; 549/51; 549/460
[58] Field of Search ................... 514/315, 317, 514/319, 320, 324, 238.8, 443, 422, 428, 468; 546/202, 248; 544/173; 549/51, 460; 548/525, 574

[56] References Cited

PUBLICATIONS

CA 106: 169032e Derivatives . . . Properties, Val'dman et al., p. 70, 1987.
CA 110: 165948t Synthesis . . . Propanols. Borisova et al., p. 61, 1989.
CA 120: 244684p N–Aryloxy(thio)alkyl–. . . Compositions, and Intermediates, Brown et al., p. 1004, 1994.
Chemical Abstracts #6017k, vol. 97 No. 1, 5 Jul. 1982, Columbus, Ohio, USA, p. 580.
Chemical Abstracts #22591d, vol. 100 No. 3, 16 Jan. 1984, Columbus, Ohio USA, p. 488.
Chemical Abstracts #209437a, vol. 100 No. 25, 18 Jun. 1984, Columbus, Ohio, USA, p. 560.
Chemical Abstracts #23366s, vol. 101 No. 3, 16 Jul. 1984, Columbus, Ohio, USA, p. 591.

*Primary Examiner*—Joseph K. McKane
*Attorney, Agent, or Firm*—Nixon & Vanderhye

[57] ABSTRACT

Heterocyclic amines of the formula $$Ar-X-A-NR^1R^2$$

wherein Ar is a bicyclic or tricyclic aromatic group which is unsubstituted or which bears one or more substituents selected from halo, nitro and cyano groups and alkyl and alkoxy groups each of up to 4 carbon atoms;
wherein X is a direct link or is —O—, —S—, —SO— or —SO$_2$— or has the formula —C(R$^3$)=CH— wherein R$^3$ is hydrogen or alkyl of up to 4 carbon atoms;
wherein A is straight or branched alkylene or alkenylene of 3 to 8 carbon atoms which may be interrupted by —O—, —S— or —NH—;
and wherein NR$^1$R$^2$ is a cyclic amino group;
or a pharmaceutically acceptable acid addition salt thereof, are of value for therapeutic use, particularly in the treatment of myocardial ischaemia and hypertension and in the treatment of fungal infections.

29 Claims, No Drawings

HETEROCYCLIC AMINES

This application is a 371 of PCT/GB93/02048 filed Oct. 1, 1993.

This invention is in the field of heterocyclic amines and in particular it relates to N-(substituted-alkyl)-cyclic amines which possess calmodulin antagonist properties. Such a compound has a cardioprotective action and finds particular use in the treatment of myocardial ischaemia and hypertension.

Calmodulin is a protein containing 148 amino acids which is found in a wide variety of tissues, including the heart. It is a receptor for calcium ions and, when bound to calcium, regulates the activity of amongst others, the enzymes phosphodiesterase, adenylate cyclase and myosin light-chain kinase and thereby influences the contraction of smooth muscle. Calmodulin also modulates the intracellular concentration of calcium ions. It is believed that in many cell systems calcium can only play its role in the presence of calmodulin, and therefore an antagonist of calmodulin acts as a calcium antagonist. The role of calmodulin is fully discussed in reviews by Means and Dedman, Nature, 1980, 285, pages 73–77; Klee et al., Annual Reviews of Biochemistry, 1980, 49, pages 489–515; and Veigl et al., Pharmacology & Therapeutics, 1989, 44, pages 181–239.

Accordingly the invention provides the use of a heterocyclic amine of the formula:

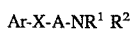

Ar-X-A-NR$^1$R$^2$ wherein Ar is a bicyclic or tricyclic aromatic group which is unsubstituted or which bears one or more substituents selected from halo, nitro and cyano groups and alkyl and alkoxy groups each of up to 4 carbon atoms;

wherein X is a direct link or is —O—, —S—, —SO— or —SO$_2$— or has the formula —C(R$^3$)=CH— herein R$^3$ is hydrogen or alkyl of up to 4 carbon atoms;

wherein A is straight or branched alkylene or alkenylene of 3 to 8 carbon atoms which may be interrupted by —O—, —S— or —NH—;

and wherein NR$^1$R$^2$ is a cyclic amino group;

or a pharmaceutically acceptable acid addition salt thereof, for the manufacture of a medicament for use in the treatment of a calmodulin-mediated disease or medical condition.

Numerous compounds have been described which incorporate a group of the formula —O—(CH$_2$)$_n$— linking an aromatic group to an amine group. In most of these compounds the linking group is only a minor part of the molecule and either the aromatic group, or the amino group, or both, are complex in nature. Furthermore, in most such compounds the linking group is —O—(CH$_2$)$_3$— and there are relatively few examples of known compounds wherein n is greater than 3. Examples of known compounds wherein there is a suggestion of activity on the cardiovascular system are:—J. Medicinal Chem., 1981, 24, 159–167 and related patent specifications DE 2730593 and FR 2431491 (complex benzofuran derivatives); EP 303920 (complex benzofuran derivatives); and WO 8905289 (4-benzylpiperidine derivatives). There is no suggestion that any of these compounds are calmodulin antagonists.

A group of Czechoslovakian patents (the contents of which are described in abstract form in Chemical Abstracts, 1983, 100, 209437; 1983, 190, 22591 and 1983, 101, 23366) describe various N-(4-naphthyloxybutyl)-cyclic amines; the only indication of utility is that their N-oxides have potential use as antimicrobials. Naphthoxyalkylamines having anti-inflammatory activity and in particular N-8-(naphth-1-yloxy)octylpyrrolidine are described in EP 82005. Thimmaiah et al., 3. Medicinal Chem., 1992, 35, 3358–3364, describe N-substituted phenoxazines and in particular various N-[4-(phenoxazin-10-yl)propyl and butyl]-cyclic amines which were studied for their ability to reverse Vinca alkaloid resistance in multidrug-resistant cancer cells. There is no suggestion that any of these compounds are calmodulin antagonists.

The compounds of the formula Ar-X-A-NR$^1$R$^2$ are heterocyclic amines, i.e. they incorporate a saturated nitrogen-containing heterocyclic ring system NR$^1$R$^2$.

The group Ar is, for example, a carbocyclic aromatic group, preferably naphthyl, anthryl, phenanthryl or fluorenyl, or a benz-heterocyclic group wherein the heterocyclic group is a 5- or 6-membered group which contains 1 or 2 heteroatoms selected from nitrogen, oxygen or sulphur atoms, for example benzo[b]thienyl, benzo[b]furyl, indolyl, quinolyl, isoquinolyl, quinazolinyl, carbazolyl or dibenzofuryl. Ar is more preferably 1- or 2-naphthyl or especially benzo[b]thienyl, for example benzo[b]thien-4-yl and benzo[b]thien-5-yl.

The group -A- is preferably a chain of the formula —(CH2)$_n$— wherein n is 3, 4, 5, 6, 7 or 8, or such a chain interrupted by one group —O—, —S— or —NH—, particularly a chain of the formula —(CH$_2$)$_m$—S—(CH$_2$)$_p$— or —(CH$_2$)$_m$—O—(CH$_2$)$_p$— wherein m is 2, 3 or 4 and p is 2, 3 or 4. More preferably the total number of atoms in the chain is no more than 6 and, especially -A- is —(CH$_2$)$_n$— wherein n is 4 or 6.

The group —NR$^1$R$^2$ is, for example, a saturated heterocyclic group wherein R$^1$ and R$^2$ are joined to form alkylene of 3 to 7 carbon atoms optionally interrupted by —O—, —S—, —NH— or —N(alkyl) wherein alkyl is of up to 4 carbon atoms, especially by one such group. More preferably —NR$^1$R$^2$ is, for example, pyrrolidino, piperidino, morpholino, piperazino, 4-methylpiperazino or hexamethyleneimino.

The group R$^3$ when it is alkyl, or for the optional alkyl substituent in Ar, is preferably methyl or ethyl.

A suitable value for the optional halo or alkoxy substituent in Ar is preferably fluoro, chloro, bromo, iodo, methoxy or ethoxy, the presence of a bromo substituent being of particular interest.

A suitable pharmaceutically acceptable acid addition salt is, for example, a salt derived from an inorganic acid, for example a hydrochloride, hydrobromide, phosphate or sulphate, or a salt derived from an organic acid, for example an oxalate, lactate, succinate, tartrate, acetate, salicylate, citrate, benzoate, beta-naphthoate or adipate.

A particularly preferred heterocyclic amine which may be used in the invention is, for example, the novel compound:

N-4-(benzo[b]thien-4-yloxy)butylpyrrolidine;
N-4-(benzo[b]thien-4-yloxy)butylpiperidine;
N-6-(benzo[b]thien-4-yloxy)hexylpyrrolidine;
N-6-(benzo[b]thien-4-yloxy)hexylpiperidine; or
N-6-(naphth-2-yl)hex-5-enylpiperidine;

or a pharmaceutically acceptable acid addition salt thereof; or the known compound:

N-4-(naphth-1-yloxy)butylpyrrolidine or a pharmaceutically acceptable acid addition salt thereof. Also of interest are the corresponding benzo[b]thien-5-yloxy compounds and especially the corresponding 3-, 5- or 7-bromo substituted benzo[b]thien-4-yloxy compounds and their benzo[b]thien-5-yloxy analogues.

The heterocyclic amines may be used in the invention in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients, using standard techniques well known to those skilled in the art of pharmacy.

The calmodulin-antagonist activity of a compound of the invention may be determined in vitro by measuring the effect of the compound in inhibiting the hydrolysis of cyclic adenosine monophosphate (cAMP) to adenosine 5'-phosphate (5'-AMP) in the presence of phosphodiesterase, calmodulin and calcium ions. The test procedure is a standard one, described by Thompson et al. in "Advances in Cyclic Nucleotide Research," 1979, 10, pages 69–106, and in principle comprises the incubation of radioactive cAMP, calmodulin, calcium chloride and phosphodiesterase (either in the absence, or presence at various concentrations, of the compound under test), followed by hydrolysis by snake venom of the radioactive 5'AMP thus formed to adenosine and assay of the radioactive adenosine. The concentration of compound which produces a 50% inhibition of phosphodiesterase activity (the $IC_{50}$) is then calculated.

The heterocyclic amine active ingredient may be used in a pharmaceutical composition together with one or more other drugs, particularly those selected from anti-cancer agents, for example adriamycin or bleomycin; sedatives, for example phenobarbitone, meprobamate, chlorpromazine and the benzodiazepine sedative drugs, for example chlordiazepoxide and diazepam; β-adrenergic blocking agents, for example atenolol and propranolol; calcium antagonists, for example nifedipine, diltiazem and verapamil; vasodilators, for example glyceryl trinitrate, pentaerythritol tetranitrate, isosorbide dinitrate and hydralazine; diuretics, for example chlorthalidone, bendrofluazide, hydrochlorothiazide and chlorothiazide; other anti-hypertensive agents, for example reserpine, bethanidine and guanethidine; cardiac membrane stabilising agents, for example quinidine; agents used in the treatment of Parkinson's disease and other tremors, for example benzhexol; cardiotonic agents, for example digitalis preparations; and alpha-adrenergic blocking agents, for example phentolamine.

According to a further feature of the invention there is provided a pharmaceutical composition which comprises as an active ingredient a heterocyclic amine of the formula:

Ar-X-A-NR$^1$R$^2$ wherein Ar is a bicyclic or tricyclic aromatic group which is unsubstituted or which bears one or more substituents selected from halo, nitro and cyano groups and alkyl and alkoxy groups each of up to 4 carbon atoms;

wherein X is a direct link or is —O—, —S—, —SO— or —SO$_2$— or has the formula —C(R$^3$)═CH— wherein R$^3$ is hydrogen or alkyl of up to 4 carbon atoms;

wherein A is straight or branched alkylene or alkenylene of 3 to 8 carbon atoms which may be interrupted by —O—, —S— or —NH—;

and wherein NR$^1$R$^2$ is a cyclic amino group;

provided that when Ar is unsubstituted naphthyl, X is —O— and -A- is —(CH$_2$)$_8$—, —NR$^1$R$^2$ is not pyrrolidino; and when Ar is phenoxazin-10-yl, X is a direct link and A is —(CH$_2$)$_3$— or —(CH$_2$)$_4$—, —NR$^1$R$^2$ is not pyrrolidino, piperidino, morpholino or N-(β-hydroxyethyl)piperazino;

or a pharmaceutically acceptable acid addition salt thereof, in association with a pharmaceutically acceptable diluent or carrier.

It will of course be appreciated that most of the compounds described hereinbefore are novel and thus the present invention extends to the following compounds per se.

According to a further feature of the invention there is provided a novel compound of the formula:

Ar-X-A-NR$^1$R$^2$ wherein Ar is a bicyclic or tricyclic aromatic group which is unsubstituted or which bears one or more substituents selected from halo, nitro and cyano groups and alkyl and alkoxy groups each of up to 4 carbon atoms;

wherein X is a direct link or is —O—, —S—, —SO— or —SO$_2$ or has the formula —C(R$^3$)═CH— wherein R$^3$ is hydrogen or alkyl of up to 4 carbon atoms;

wherein A is straight or branched alkylene or alkenylene of 4 to 8 carbon atoms which may be interrupted by —O—, —S— or —NH—; and wherein NR$^1$R$^2$ is a cyclic amino group;

provided that when Ar is unsubstituted naphthyl, X is —O— and -A- is —(CH$_2$)4—, —NR$^1$R$^2$ is not pyrrolidino, piperidino, hexamethyleneimino or morpholino; when Ar is unsubstituted naphthyl, X is —O— and -A- is —(CH$_2$)$_8$—, —NR$^1$R$^2$ is not pyrrolidino;

and when Ar is phenoxazin-10-yl, X is a direct link and A is —(CH$_2$)$_3$— or —(CH$_2$)$_4$—, NR$^1$R$^2$ is not pyrrolidino, piperidino, morpholino or N-(β-hydroxyethyl)piperazino;

or a pharmaceutically acceptable acid addition salt thereof.

The novel compounds of the invention may be prepared by any process known for the preparation of chemically-related compounds. Accordingly, certain such processes form a further feature of the invention.

According to a further feature of the invention there is provided a process for the manufacture of a novel compound of the invention which comprises the reaction of a compound of the formula:

Ar-X-A-Z wherein Ar, X and A have the meanings stated above and wherein Z is a displaceable group, for example a halo or sulphonyloxy group such as the bromo or tosyl group, with an amine of the formula HNR$^1$R$^2$, wherein R$^1$ and R$^2$ have the meanings stated above.

According to a further feature of the invention there is provided a process for the manufacture of a novel compound of the invention which comprises the reduction of an amide of the formula:

Ar-X-A$^1$-CO—NR$^1$R$^2$ wherein Ar, X, R$^1$ and R$^2$ have the meanings stated above and wherein A$^1$ is such that A$^1$-CH$^2$ has the same meaning as stated above for A.

The reduction may be carried out using a complex metal hydride, for example lithium aluminium hydride, by known techniques. The amide starting material may be obtained by reacting an activated derivative of the corresponding carboxylic acid with an amine of the formula HNR¹R² wherein R¹ and R² have the meanings stated above.

According to a further feature of the invention there is provided a process for the manufacture of a novel compound of the invention wherein X has the formula —CR³=CH— which comprises the dehydration of a compound of the formula:

Ar-CR³(OH)—CH²-A-NR¹R² wherein Ar, X, R¹, R² and R³ have the meanings stated above.

The processes described above for the preparation of the novel compounds of the invention may also be applied to the synthesis of compounds of use in the invention which are not novel per se.

The invention may find use in the treatment of cancer or of psoriasis but finds particular use for the treatment of myocardial ischaemia or the treatment of hypertension in man. It is also of interest for the treatment of fungal infections, particularly those caused by yeasts, especially *Candida* species. Compounds containing a bromo substituted benzo[b]thienyl group Ar have been found to be of particular interest in this context.

It will be appreciated that the anti-fungal activity and possibly also the anti-psoriasis activity may, at least in part, be attributable to other than the calmodulin antagonist activity of the compounds of the invention. It will be appreciated that the invention extends to the use of the compounds described herein in such a context even if the activity of the compounds as anti-fungal or anti-psoriasis agents is not attributable to their calmodulin antagonist activity.

According to a further feature of the invention there is provided a heterocyclic amine of the formula:

Ar-X-A-NR¹R² wherein Ar is a bicyclic or tricyclic aromatic group which is unsubstituted or which bears one or more substituents selected from halo, nitro and cyano groups and alkyl and alkoxy groups each of up to 4 carbon atoms;

wherein X is a direct link or is —O—, —S—, —SO— or —SO₂— or has the formula —C(R³)=CH— wherein R³ is hydrogen or alkyl of up to 4 carbon atoms;

wherein A is straight or branched alkylene or alkenylene of 3 to 8 carbon atoms which may be interrupted by —O—, —S— or —NH—;

and wherein NR¹R² is a cyclic amino group;

provided that when Ar is unsubstituted naphthyl, X is —O— and -A- is —(CH₂)₈—, —NR¹R² is not pyrrolidino; and when Ar is phenoxazin-10-yl, X is a direct link and A is —(CH₂)₃— or —(CH₂)₄—, —NR¹R² is not pyrrolidino, piperidino, morpholino or N-(β-hydroxyethyl)piperazino;

or a pharmaceutically acceptable acid addition salt thereof, for use in a method of treatment of the human or animal body by therapy.

When used for the treatment of myocardial ischaemia or for the treatment of hypertension in man, it is expected that the pharmaceutical composition of the invention would be administered such that the heterocyclic amine would be given to man at a total oral dose of between 20 mg and 600 mg daily or an intravenous dose of between 1 mg and 20 mg.

Doses within these ranges may in general be used for the treatment of cancer, psoriasis or fungal infections, topical application of the compounds being of particular interest in the treatment of psoriasis and of fungal infections. However, therapeutically effective doses outside the ranges may be used where appropriate.

Preferred oral dosage forms are tablets or capsules containing between 10 and 100 mg, and preferably 10 mg or 50 mg, of active ingredient. Preferred topical dosage forms are compositions containing similar amounts to the oral dosage forms within a volume of 1 to 10 ml. Preferred intravenous dosage forms are sterile solutions of the basic ether or of a non-toxic acid addition salt thereof, containing between 0.05% and 1% w/v of active ingredient, and more particularly containing 0.1% w/v of active ingredient.

According to a further feature of the invention there is provided a method for the treatment of myocardial ischaemia, hypertension or a fungal infection in a warm-blooded animal in need of such treatment which comprises administering to said warm-blooded animal an effective amount of a compound of the formula:

Ar-X-A-NR¹R² wherein Ar, is a bicyclic or tricyclic aromatic group which is unsubstituted or which bears one or more substituents selected from halo, nitro and cyano groups and alkyl and alkoxy groups each of up to 4 carbon atoms;

wherein X is a direct link or is —O—, —S—, —SO— or —SO₂— or has the formula —C(R³)=CH— wherein R³ is hydrogen or alkyl of up to 4 carbon atoms;

wherein A is straight or branched alkylene or alkenylene of 3 to 8 carbon atoms which may be interrupted by —O—, —S— or —NH—;

and wherein NR¹R² is a cyclic amino group;

or a pharmaceutically acceptable acid addition salt thereof.

The invention will now be illustrated by way of example only.

EXAMPLE 1

A solution of 4-(naphth-1-yloxy)-N,N-pentamethylenebutyramide (1.5 g) in tetrahydrofuran (THF, 50 ml) was added dropwise to a stirred suspension of lithium aluminium hydride (LAH, 1.0 g) in diethyl ether (DEE, 50 ml) under an atmosphere of nitrogen, and the mixture was stirred and heated under reflux for 2 hours, stirred at laboratory temperature for 1 hour, diluted with DEE and an excess of a mixture of ethyl acetate and DEE (sufficient to decompose any residual LAH) was added. Aqueous 4M-sodium hydroxide solution was added until a white precipitate formed and the mixture was filtered. The solid was washed with THF and the combined filtrate and washings were dried over sodium sulphate and evaporated to dryness. The residue was dissolved in ethanol and a solution of oxalic acid in ethanol was added. The mixture was filtered and the solid product was crystallised from ethanol. There was thus obtained -4-(naphth-1-yloxy)butylpiperidine oxalate, m.p. 196.5°–197° C. The butyramide used as starting material was obtained as follows:

1-Naphthol (14.4 g) and a solution of ethyl 4-bromobutyrate (20.9 g) in ethanol (50 ml) were successively added to a stirred solution of sodium (2.3 g) in ethanol (100 ml) and the mixture was heated under reflux for 7 hours, filtered hot and the filtrate was evaporated to dryness. The residue was partioned between water and ethyl acetate and the organic layer was washed with aqueous molar ammonia solution, dried and evaporated to dryness. To the residue was added a solution of sodium hydroxide (10 g) in a mixture of water (100 ml) and ethanol (50 ml) and the mixture was stirred and heated under reflux for 4 hours, cooled, acidified with concentrated hydrochloric acid and filtered. The solid residue was crystallised from toluene and there was thus obtained 4-(naphth-1-yloxy)butyric acid, m.p. 119°–121.5° C.

Triethylamine (1.4 ml) and ethyl chloroformate (1.1 ml) were successively added to a stirred solution of 4-(naphth-1-yloxy)butyric acid (2.44 g) in dry THF (20 ml) at 0° C. Piperidine (2.0 ml) was then added and the stirred mixture was allowed to warm up to laboratory temperature and was then filtered. The filtrate was evaporated to dryness and the residue was partitioned between molar aqueous ammonia solution and DEE. The ethereal solution was dried over sodium sulphate, evaporated to dryness and the butyramide product was purified by flash chromatography on a silica gel (Merck 9385) column using ethyl acetate as eluant.

EXAMPLE 2

The process described in Example 1 was repeated using the appropriate amide as starting material and there were thus obtained the compounds described in the following table:

hydride was destroyed by the addition of ethanol. The mixture was filtered, the filtrate was evaporated to dryness and the residue was dissolved in aqueous 2N-sodium hydroxide solution. The mixture was filtered, the filtrate was acidified with hydrochloric acid and the mixture was filtered. The solid residue was crystallised from chloroform and there was thus obtained 4-(naphth-2-ylthio)butyric acid, m.p. 122° C.

The acids were converted into amides by a similar process to that described in Example 1.

Note 3. 8-(Naphth-1-yloxy)octanoic acid was prepared as follows:

8-Bromo-octanoic acid (4.46 g) was added to a stirred solution of 1-naphthol (2.88 g) and potassium hydroxide (2.8 g) in water (30 ml) and the mixture was heated under reflux for 6 hours and then acidified with concentrated hydrochloric acid. The mixture was evaporated with DEE and the extract was dried over sodium sulphate and evaporated to dryness. The residue was heated with petroleum ether, the solvent layer was decanted off and cooled and the mixture was filtered. There was thus obtained 8-(naphth-1-yloxy)octanoic acid, m.p. 76°–79° C.

The naphthylthioalkanoic acids were similarly prepared except that the DEE extraction step was unnecessary; the

| | | Ar-X-A-NR$^1$R$^2$ | | | |
|---|---|---|---|---|---|
| Ar | X A | NR$^1$R$^2$ | salt | m.p. °C. | note |
| naphth-1-yl | O -(CH$_2$)$_5$- | piperidino | HCl | 181–182.5 | 1 |
| naphth-1-yl | O -(CH$_2$)$_6$- | piperidino | HCl | 160–162.5 | 2 |
| naphth-1-yl | O -(CH$_2$)$_8$- | piperidino | HCl | 170–170.5 | 3 |
| naphth-2-yl | O -(CH$_2$)$_3$- | piperidino | HCl | 196–198 | 2 |
| naphth-1-yl | O -(CH$_2$)$_5$- | morpholino | HCl | 189–190.5 | 1 |
| 6-bromo-naphth-2-yl | O -(CH$_2$)$_4$- | piperidino | HCl | 223–225 | 2 |
| naphth-1-yl | O -(CH$_2$)$_2$SCH$_2$- | piperidino | Ox | 173–175 | 4 |
| naphth-1-yl | S -(CH$_2$)$_4$- | piperidino | Ox | 163–165 | 2 |
| naphth-2-yl | S -(CH$_2$)$_4$- | piperidino | Ox | 139.5–142 | 2 |
| naphth-2-yl | S -(CH$_2$)$_5$- | piperidino | Ox | 153–154 | 3 |
| naphth-2-yl | S -(CH$_2$)$_6$- | piperidino | HCl | 145.5–147.5 | 3 |
| naphth-2-yl | S -(CH$_2$)$_4$- | pyrrolidino | Ox | 132.5–134.5 | 2 |
| naphth-2-yl | S -(CH$_2$)$_5$- | morpholino | Ox | 166.5–168.5 | 3 |
| dibenzofur-2-yl | O -(CH$_2$)$_4$- | piperidino | HCl | 183.5–185 | 2 |

The starting materials for the compounds described in the above table were prepared from the appropriate aromatic -ol or -thiol by similar processes to those described in the second part of Example 1, by reaction with the appropriate ω-haloalkanoic acid or ester followed by amide formation by the mixed anhydride route as described in Example 1 or by a conventional carbodiimide reaction. Details are as described in the following notes.

Note 1. The aryloxyalkanoic acid was prepared by a similar process to that described in Example 1 and the amide was prepared therefrom also by a similar process to that described in Example 1.

Note 2. The aryloxy- or arylthio-alkanoic acid was prepared by a process exemplified by the following preparation of 4-(naphth-2-ylthio)butyric acid:

A solution of 2-thionaphthol (0.48 g) in N,N-dimethylformamide (DMF, 10 ml) and a solution of 4-bromobutyric acid (0.5 g) in DMF (5 ml) were successively added to a stirred suspension of sodium hydride (0.23 g) in DMF (5 ml) and the mixture was heated under reflux for 4 hours, cooled and the excess of sodium acids were filtered off directly from the acidified aqueous reaction mixture.

The acids were converted into amides by reaction with piperidine or morpholine in the presence of dicyclohexylcarbodiimide (DCCI) and hydroxybenzotriazole (HOBT) by standard amide formation methods.

Note 4. 2-[(Naphth-1-yloxy)ethylthio]acetic acid was prepared as follows:

Methylthioglycolate (0.45 ml) was added to a stirred solution of sodium (0.12 g) in methanol (50 ml) and the solution was evaporated to dryness. 2-(Naphth-1-yloxy)ethyl bromide (1.26 g; prepared from 1-naphthol and dibromomethane by a similar process to that described hereinafter in the second part of Example 3) was added to a stirred solution of the residue in DMF (15 ml) and the mixture was kept at laboratory temperature for 16 hours and then evaporated to dryness. To the residue was added a mixture of 2N-aqueous sodium hydroxide solution (10 ml) and ethanol (10 ml) and the mixture was heated under reflux for 3 hours and then evaporated to dryness. A solution of the residue in hot water was acidified with concentrated aqueous hydrochloric acid and extracted with dichloromethane. The extract was dried over sodium sulphate and evaporated to dryness. The residue was crystallised from cyclohexane and there was thus obtained 2-[(naphth-1-yloxy)ethylthio]acetic acid, m.p. 64.5°–65.5° C.

The acid was converted into the amide by reaction with piperidine in the presence of DCCI and HOBT.

EXAMPLE 3

A solution of 4-(4-bromobutyloxy)benzo[b]thiophen (1.43 g) in THF (30 ml) was added to a stirred solution of piperidine (1.5 ml) in THF (10 ml) and the mixture was stirred at laboratory temperature for 17 hours and then evaporated to dryness. The residue was partitioned between DEE and dilute hydrochloric acid and the aqueous layer was basified and extracted with dichloromethane. The extract was dried over sodium sulphate and evaporated to dryness and the residue was dissolved in ethanol. A solution of oxalic acid in ethanol was added, the mixture was filtered and the solid product was crystallised from water. There was thus obtained N-[4-(benzo[b]thien-4-yloxy)butyl]piperidine oxalate, m.p. 188.5°–189° C.

The starting material was obtained as follows:

1,4-Dibromobutane (20.9 ml), tetrabromobutylammonium bromide (1 g), water (150 ml) and aqueous 50% sodium hydroxide solution (50 ml) were successively added to a stirred solution of benzo[b]thiophen-4-ol (5.25 g) in dichloromethane (200 ml) and the mixture was vigorously stirred at laboratory temperature for 2 days. The organic layer was separated and evaporated to dryness and the excess of dibromobutane was removed by distillation. The residue was purified by chromatography on a silica gel column using dichloromethane as eluant and there was thus obtained 4-(4-bromobutyloxy)benzo[b]thiophen as an oil.

EXAMPLE 4

The process described in Example 3 was repeated using the appropriate bromoalkyloxythiophen (prepared as described in the second part of Example 3) and the appropriate amine as starting materials and there were thus obtained the compounds described in the following table:

sulphuric acid. The aqueous layer was separated, basified and extracted with dichloromethane and the extract was dried over sodium sulphate and evaporated to dryness. The crude amine obtained as residue was converted into its hydrochloride with a solution of hydrogen chloride in DEE and there was thus obtained N-7-(naphth-1-yloxy)heptylpiperidine hydrochloride, m.p. 149.5°–151° C.

EXAMPLE 6

Boron trifluoride etherate (1.79 ml) was added to a stirred solution of N-(5-piperidinopentyl)naphth-1-ylacetamide (5.1 g) in THF (15 ml) which was maintained under an atmosphere of dry nitrogen, and the mixture was heated under reflux. Borane-dimethyl sulphide (1.6 ml) was added during 10 minutes and the THF and other volatile materials were distilled off during 30 minutes. Aqueous 4N-hydrochloric acid (20 ml) was added and the mixture was heated under reflux for 1 hour, cooled and basified. An excess of potassium carbonate was added and the mixture was extracted with 3–100 ml DEE. The extract was dried over sodium sulphate and evaporated to dryness. The residue was redissolved in DEE and a solution of hydrogen chloride in DEE was added. The mixture was filtered and the product was crystallised from ethanol. There was thus obtained N-5-[2-(naphth-1-yl)ethylamino]pentylpiperidine hydrochloride, m.p. 192.5°–194° C.

The amide used as starting material was prepared from naphth-1- ylacetic acid and 5-piperidinopentylamine in the presence of dicyclohexylcarbodiimide and hydroxybenzotriazole by standard means.

EXAMPLE 7

A mixture of 1-(naphth-2-yl)-6-piperidinohexan-1-ol (0.5 g) and a 6% w/v solution of oxalic acid in water (25 ml) was stirred and heated under reflux for 7 hours, cooled and filtered. The solid product was crystallised from ethanol and there was thus obtained N-6-(naphth-2-yl)hex-5-enylpiperidine oxalate, m.p. 184.5°–185.5° C.

The starting material was obtained from 5-(naphth-2-oyl)valeric acid by piperidine amide formation using ethyl chloroformate (by a similar process to that described in the second part of Example 1; 5-(naphth-2-oyl)-N,N-pentam-

| | Ar-X-A-NR$^1$R$^2$ | | | | |
| Ar | X | A | NR$^1$R$^2$ | salt | m.p. °C. |
| --- | --- | --- | --- | --- | --- |
| benzo[b]thien-4-yl | O | -(CH$_2$)$_4$- | pyrrolidino | Ox | 181–182.5 |
| benzo[b]thien-4-yl | O | -(CH$_2$)$_6$- | piperidino | Ox | 117.5–120 |
| benzo[b]thien-4-yl | O | -(CH$_2$)$_6$- | pyrrolidino | Ox | 138–141 |
| 3-bromobenzo[b]thien-4-yl | O | -(CH$_2$)$_6$- | pyrrolidino | Ox | 142–145 |
| 5-bromobenzo[b]thien-4-yl | O | -(CH$_2$)$_6$- | pyrrolidino | Ox | 136–140 |
| 7-bromobenzo[b]thien-4-yl | O | -(CH$_2$)$_6$- | pyrrolidino | Ox | 136–140 |
| benzo[b]thien-5-yl | O | -(CH$_2$)$_4$- | pyrrolidino | Ox | 170–171.5 |
| benzo[b]thien-5-yl | O | -(CH$_2$)$_6$- | pyrrolidino | Ox | 174–175 |

EXAMPLE 5

A solution of N-(1-butoxymethyl)piperidine (2.3 g; prepared from piperidine and paraformaldehyde by the method described in J. Am. Chem. Soc., 1940, 62, 1450–2) in 50 ml DEE was added to a stirred Grignard reagent prepared by standard techniques from magnesium (0.36 g) and 6-(naphth-1-yloxy)hexyl bromide (4.6 g) in 50 ml DEE which was heated under reflux, and the mixture was heated under reflux for 30 minutes and cooled. Aqueous 10% sulphuric acid was added, the mixture was filtered and the filtrate was partitioned between DEE and aqueous 10% ethylenevaleramide has m.p. 70.6°–72.1° C. after crystallisation from cyclohexane) followed by lithium aluminium hydride reduction (by a similar process to that described in the first part of Example 1).

EXAMPLE 8

3-Bromo-1-propanol (1.67 g) was added to a stirred solution of 4-hydroxybenzo[b]thiophene (1.50 g) and potassium carbonate (3.04 g) in 2-butanone (40 ml) under an atmosphere of nitrogen and the mixture was heated under reflux for 3 hours. The mixture was filtered and the filtrate evaporated to dryness. The solid residue was recrystallised from ethanol to give 4-(3-hydroxypropyloxy)benzo[b]thiophene of m.p. 82° C. A solution of N-chloroacetylpyrrolidine (1.47 g) in tetrahydrofuran (THF, 10 ml) was added in one portion to a stirred solution of 4-(3-hydroxypropyloxy)benzo[b]thiophene (1.75 g) and sodium hydride (60% suspension, 0.40 g) in tetrahydrofuran under an atmosphere of nitrogen and stirring was continued for 1 hour at room temperature. The solution was filtered and the filtrate evaporated to afford an oil, which was purified by flash chromatography (silica, ethylacetate:petroleum, 1:1 v/v) to yield the pyrrolidine amide of 3-(4-benzothiophenoxy)propyloxy acetic acid.

The amide was reduced with lithium aluminium hydride to give the corresponding amine, N-[6-(benzo[b]thien-4-yloxy)-3-oxahexyl]pyrrolidine, isolated as the mono-oxalate salt by the procedure described in Example 1 with m.p. 180.5°–183.0° C.

EXAMPLE 9

The pyrrolidine amide of 3-(6-bromonaphth-2-yloxy)propyloxy acetic acid was prepared from N-chloroacetylpyrrolidine and 3-(6-bromonaphth-2-yloxy)propan-1-ol by the procedure described in Example 8. The amide was reduced with borane-dimethyl sulphide by the procedure described in Example 6 to give the corresponding amine, N-[6-(6-bromonaphth-2- yloxy)-3-oxahexyl] pyrrolidine, isolated as the mono-oxalate salt by the procedure described in Example 1 with m.p. 208°–211° C.

EXAMPLE 10

A mixture of N-4-(naphth-1-yloxy)butylpyrrolidine oxalate (50 parts by weight), lactose (182.5 parts by weight) and maize starch (12.5 parts by weight) was blended, magnesium stearate (2.5 parts by weight) and stearic acid (2.5 parts by weight), each of which had been passed through a 60-mesh sieve, were added and the mixture was compressed into tablets each weighing 250 mg. There were thus obtained tablets containing 50 mg of active ingredient suitable for human use for therapeutic purposes.

EXAMPLE 11

Evaluation of the potency of synthetic inhibitors of calmodulin cannot be achieved directly; calmodulin is a protein which modulates enzyme activity, it does not have an inherent activity. The most widely used method for determining the inhibitory effects of drugs on calmodulin is the assay of calmodulin-dependent cyclic nucleotide phosphodiesterase (PDE) (Thompson et al., Advances in Cyclic Nucleotide Research, 1979, 10, 69–106.

The assay was based on the incubation of calmodulin-deficient bovine heart PDE with [$^3$H] cyclic adenosine monophosphate (cAMP), and a sufficient amount of bovine brain calmodulin (12.5 ng/100 µl) to give 70–80% activation of the enzyme. The resultant [$^3$H] 5'-AMP formed was hydrolysed to [3H] adenosine upon incubation with the 5'-nucleotidase of the Western Diamondback Rattlesnake (*Crotalus atrox*). The nucleoside was then separated from the unreacted substrate using anion exchange resin. The amount of adenosine formed, measured by the amount of radioactivity present, was proportional to the activity of calmodulin-activated PDE and hence the inhibition of calmodulin. The degree of inhibition of calmodulin-activation of PDE in the presence of a range of drugs was expressed as a percentage of the activity of calmodulin-activated PDE in the absence of any drug.

To obtain a reliable $IC_{50}$ [concentration of drug at which 50% inhibition is seen], graphs were plotted on the average percentage inhibition of calmodulin-activation of PDE (from n=3) versus the concentration of drug present. From these plots the $IC_{50}$ was determined. To obtain the quoted $IC_{50}$ value for each compound, each assay was repeated at least three times on separate occasions and the mean±S.E. calculated. In certain stated cases, only two assays were completed.

Dimethyl sulphoxide was used as an initial solvent for the compounds, resulting in a 2% (v/v) final concentration in the assay, affecting the basal and calmodulin-activated activity of PDE by approximately 10%. To obtain a true reflection of the effect of each compound it was these solvent-modified activities that were used to determine the percentage inhibition of calmodulin.

As a large number of the compounds prepared were isolated as their oxalate salts, an assay was undertaken with oxalic acid at various concentrations to observe any effect on calmodulin-activated PDE and PDE; none was found.

In an effort to increase the reliability of each assay, an internal standard, IODO8, was used; at a concentration of 3 µM this drug should give between 40–60% inhibition.

There is evidence that certain inhibitors of calmodulin-activated PDE may also inhibit the calmodulin-independent activity of PDE. To give an indication of any inhibition of PDE by compounds, the activity of PDE in the presence of two concentrations of compound (approximately ten fold difference) were included in the assay. As there was no significant difference in the activity of PDE with or without the drug it was concluded that there was no inhibition of calmodulin-independent PDE by the drugs at the concentrations used. The percentage inhibition recorded for calmodulin-activated PDE was therefore due solely to the action of the drugs on the activity of calmodulin.

The preparation of the anion exchange resin for use in the assay was modified. Previously the resin was washed successively with 0.5M HCl, water, aqueous NaOH (0.5M) and water five times, the resin then repeatedly washed with water until a pH of 5 was obtained. Problems were encountered using this method and it was adapted by using 2M HCl and aqueous NaOH to give a more efficient wash. The pH of local distilled water was consistently found to be less than pH 5; the resin was thus washed until a constant pH was obtained, usually pH 4.

The results are shown in the following Tables. Where * is shown, this signifies that a mean of two instead of three results was taken.

TABLE 1

$X(CH_2)_nN$

| substitution | linkage X | no. of carbons | no. of atoms | $IC_{50}$ in µM(x ± SE) |
|---|---|---|---|---|
| α | 0 | 5 | 6 | 39.1 ± 8.9 |
| β | S | 5 | 6 | 22.1 ± 3.0 |
| β | CH=CH | 4 | 6 | 2.2 ± 0.3* |

TABLE 2

The effect of side chain length and substitution on calmodulin antagonist activity

| substitution | n = | X = | IC$_{50}$ in μM(x ± SE) |
|---|---|---|---|
| α | 2 | CH$_2$ | 152.1 ± 18.8 |
| α | 3 | CH$_2$ | 106.1 ± 18.0* |
| α | 4 | CH$_2$ | 7.4 ± 0.5 |
| α | 5 | CH$_2$ | 39.1 ± 8.9 |
| α | 6 | CH$_2$ | 28.5 ± 2.0 |
| α | 7 | CH$_2$ | 4.7 ± 0.3 |
| α | 8 | CH$_2$ | 5.3 ± 0.3 |
| β | 2 | CH$_2$ | >250* |
| β | 3 | CH$_2$ | 29.2 ± 1.4* |
| β | 4 | CH$_2$ | 55.8 ± 6.0 |
| β | 5 | CH$_2$ | 53.9 ± 1.6 |
| α | 2 | O | >>250 |
| α | 3 | O | 217.0 ± 24.7* |
| α | 4 | O | 53.2 ± 10.5 |
| α | 5 | O | 42.3 ± 9.1 |
| β | 2 | O | >>250* |
| β | 3 | O | >>250 |
| β | 4 | O | 85.6 ± 7.0 |
| β | 5 | O | 72.7 ± 9.4 |

These results show that for optimum antagonist activity, chain length is preferably n>3 and that for a given chain length, α naphthyl compounds are more potent than the corresponding β compounds. Amines of high basicity (e.g. piperidine) are more effective than those of moderate basicity (e.g. morpholine).

TABLE 3

The effect of side chain length and substitution of thionaphthyloxyalkylamines on calmodulin antagonistic activity

| substitution | n = | R = | IC$_{50}$ in μM(x ± SE) |
|---|---|---|---|
| β | 3 | piperdine | 77.7 ± 4.1 |
| β | 4 | piperdine | 12.3 ± 2.6 |
| β | 5 | piperdine | 22.1 ± 3.0 |
| β | 6 | piperdine | 12.5 ± 1.5* |
| β | 4 | pyrrolidine | 18.0 ± 1.3 |
| β | 5 | morpholine | 20.1 ± 2.25 |
| α | 4 | piperdine | 23.6 ± 1.6 |

This table shows that potent inhibitors can be obtained on replacing O by S in a given series.

TABLE 4

The effect of heteroatoms in the side chain of calmodulin antagonists on their inhibition of calmodulin

| | IC$_{50}$ in μM(x ± SE) |
|---|---|
| 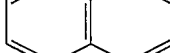 | 41.7 ± 6.2 |
|  | 11.5 ± 1.6 |

Where * signifies that a mean of two results instead of three was taken.

This table shows that the incorporation of a heteroatom into the side chain does not affect the antagonistic activity of a series of compounds.

TABLE 5

The effect of base strength of the terminal amine on calmodulin inhibition

| amine:- | IC50 in μM (x ± S.E.) | pka |
|---|---|---|
| NH$_2$ | 3.85 ± 0.2 | 10.64 |
| pyrrolidine | 4.0 ± 0.2 | 10.32 |
| piperidine | 7.4 ± 0.5 | 10.08 |
| morpholine | 53.2 ± 10.5 | 7.41 |
| imidazole | 68.3 ± 6.7 | 7.33 |

As the base strength of the terminal amine increases so does the potency of the calmodulin antagonist.

TABLE 6

The effect of halogen substitution on the naphthalene ring on calmodulin antagonist activity

| | IC$_{50}$ in μM(x ± SE) |
|---|---|
| 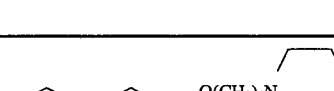 | 55.8 ± 6.0 |
| 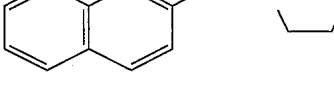 | 9.3 ± 2.0 |

TABLE 7

The effect of the aryl moiety on calmodulin antagonist activity

| n = | R = | IC$_{50}$ in μM (x ± SE) |
|---|---|---|

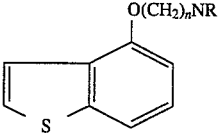

| 4 | piperdine | 1.8 ± 0.6 |
| 4 | pyrrolidine | 0.88 ± 0.14 |
| 6 | piperdine | 0.38 ± 0.10 |
| 6 | pyrrolidine | 0.22 ± 0.04 |

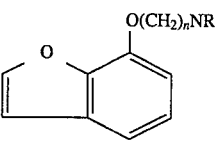

| 4 | piperdine | 70.1 ± 8.6 |
| 6 | pyrrolidine | 204.4 ± 13.3* |

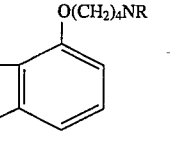

19.6 ± 2.9

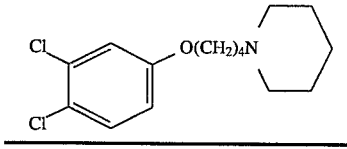

55.3 ± 10.0

We claim:

1. A pharmaceutical composition which comprises as an active ingredient a heterocyclic amine of the formula Ar-X-A-NR$^1$R$^2$ wherein Ar is a bicyclic or tricyclic aromatic group which is unsubstituted or which bears one or more substituents selected from halo, nitro and cyano groups and alkyl and alkoxy groups each of up to 4 carbon atoms;

wherein X is a direct link or is —O—, —S—, —SO— or —SO$_2$— or has the formula —C(R$^3$)=CH— wherein R$^3$ is hydrogen or alkyl of up to 4 carbon atoms;

wherein A is straight or branched alkylene or alkenylene of 3 to 8 carbon atoms which may be interrupted by —O—, —S— or —NH—;

and wherein NR$^1$R$^2$ is a cyclic amino group;

provided that when Ar is naphthyl or naphthyl substituted by halo, alkoxy or alkyl, X is —O— and A is (CH$_2$)$_{3-8}$, R$^1$R$^2$ of the cyclic amine group does not form an alkylene group; and when Ar is phenoxazin-10-yl, X is a direct link and A is —(CH$_2$)$_3$— or —(CH$_2$)$_4$—, —NR$^1$R$^2$ is not pyrrolidino, piperidino, morpholino or N-(β-hydroxyethyl)piperazino; or a pharmaceutically acceptable acid addition salt thereof, in association with a pharmaceutically acceptable diluent or carrier.

2. A pharmaceutical composition according to claim 1 wherein Ar is a carbocyclic aromatic group.

3. A pharmaceutical composition according to claim 1 wherein Ar is naphthyl, anthryl, phenanthryl or fluorenyl, or a benz-heterocyclic group wherein the heterocyclic group is a 5- or 6-membered group which contains 1 or 2 heteroatoms selected from nitrogen, oxygen or sulphur atoms, including benzo[b]thienyl, benzo[b]furyl, indolyl, quinolyl, isoquinolyl, quinazolinyl, carbazolyl or dibenzofuryl.

4. A pharmaceutical composition according to claim 3 wherein Ar is naphthyl.

5. A pharmaceutical composition according to claim 3 wherein Ar is benzo[b]thienyl.

6. A pharmaceutical composition according to claim 1 wherein A is a chain of the formula —(CH$_2$)$_n$— wherein n is 3, 4, 5, 6, 7 or 8, or a chain of the formula —(CH$_2$)$_m$—S—(CH$_2$)$_p$— or —(CH$_2$)$_m$—O—(CH$_2$)$_p$— wherein m is 2, 3 or 4 and p is 2, 3 or 4.

7. A pharmaceutical composition according to claim 6 wherein A is a group —(CH$_2$)$_n$— wherein n is 4 or 6.

8. A pharmaceutical composition according to claim 1 wherein the group —NR$^1$R$^2$ is a group wherein R$^1$ and R$^2$ are joined to form alkylene of 3 to 7 carbon atoms optionally interrupted by —O—, —S—, —NH— or —N(alkyl) wherein alkyl is of up to 4 carbon atoms.

9. A pharmaceutical composition according to claim 8 wherein —NR$^1$R$^2$ is pyrrolidino, piperidino, morpholino, piperazino, 4-methylpiperazino or hexamethyleneimino.

10. A pharmaceutical composition according to claim 1 wherein X is a group —C(R$^3$)=CH—.

11. A pharmaceutical composition according to claim 10 wherein R$^3$ is methyl or ethyl.

12. A pharmaceutical composition according to claim 1 wherein the Ar group is substituted by one or more of an alkyl group, a halo group or an alkoxy group.

13. A pharmaceutical composition according to claim 12 wherein the alkyl substituent is methyl or ethyl.

14. A pharmaceutical composition according to claim 12 wherein the halo group is fluoro, chloro, bromo or iodo.

15. A pharmaceutical composition according to claim 12 wherein the alkoxy group is methoxy or ethoxy.

16. A pharmaceutical composition according to claim 1 wherein the active ingredient is any one of N-4-(benzo[b]thien-4-yloxy)butylpyrrolidine;
N-4-(benzo[b]thien-4-yloxy)butylpiperidine;
N-6-(benzo[b]thien-4-yloxy)hexylpyrrolidine;
N-6-(benzo[b]thien-4-yloxy)hexylpiperidine; or
N-6-(naphth-2-yl)hex-5-enylpiperidine;

or a pharmaceutically acceptable acid addition salt thereof.

17. A pharmaceutical composition according to claim 1 wherein the active ingredient is any one of:

N-4-(3-bromobenzo[b]thien-4-yloxy)butylpyrrolidine;
N-4-(3-bromobenzo[b]thien-4-yloxy)butylpiperidine;
N-6-(3-bromobenzo[b]thien-4-yloxy)hexylpyrrolidine;
N-6-(3-bromobenzo[b]thien-4-yloxy)hexylpiperidine;
N-4-(5-bromobenzo[b]thien-4-yloxy)butylpyrrolidine;
N-4-(5-bromobenzo[b]thien-4-yloxy)butylpiperidine;
N-6-(5-bromobenzo[b]thien-4-yloxy)hexylpyrrolidine;
N-6-(5-bromobenzo[b]thien-4-yloxy)hexylpiperidine;
N-4-(7-bromobenzo[b]thien-4-yloxy)butylpyrrolidine;
N-4-(7-bromobenzo[b]thien-4-yloxy)butylpiperidine;
N-6-(7-bromobenzo[b]thien-4-yloxy)hexylpyrrolidine; or
N-6-(7-bromobenzo[b]thien-4-yloxy)hexylpiperidine;

or a pharmaceutically acceptable acid addition salt thereof.

18. A pharmaceutical composition according to claim 1 adapted for oral administration.

19. A pharmaceutical composition according to claim 1 adapted for topical administration.

20. A pharmaceutical composition according to claim 1 adapted for nasal administration.

21. A pharmaceutical composition according to claim 1 adapted for vaginal or rectal administration.

22. A pharmaceutical composition according to claim 1 adapted for parenteral administration.

23. A pharmaceutical composition according to claim 1 further comprising one or more drugs selected from anti-cancer agents, sedatives, calcium antagonists, diuretics, antihypertensive agents, cardiac membrane stabilising agents, cardiotonic agents and alpha-adrenergic blocking agents.

24. A heterocyclic amine of the formula:

Ar-X-A-NR$^1$R$^2$ wherein Ar, X, A, R$^1$ and R$^2$ are as defined in claim 1, or a pharmaceutically acceptable acid addition salt thereof.

25. A method for the treatment of myocardial ischaemia, hypertension or a fungal infection in a warm-blooded animal in need of such treatment which comprises administering to said warm-blooded animal a therapeutically effective amount of a heterocyclic amine of the formula:

Ar-X-A-NR$^1$R$^2$ wherein Ar is a bicyclic or tricyclic aromatic group which is unsubstituted or which bears one or more substituents selected from halo, nitro and cyano groups and alkyl and alkoxy groups each of up to 4 carbon atoms;

wherein X is a direct link or is —O—, —S—, —SO— or —SO$_2$— or has the formula —C(R$^3$)=CH— wherein R$^3$ is hydrogen or alkyl of up to 4 carbon atoms;

wherein A is straight or branched alkylene or alkenylene of 3 to 8 carbon atoms which may be interrupted by —O—, —S— or —NH—;

and wherein NR 1R is a cyclic amino group;

or a pharmaceutically acceptable acid addition salt thereof.

26. A method according to claim 24, wherein Ar, X, A, R$^1$ and R$^2$ are as defined above.

27. A heterocyclic amine of the formula:

Ar-X-A-NR$^1$R$^2$ wherein Ar is a bicyclic or tricyclic aromatic group which is unsubstituted or which bears one or more substituents selected from halo, nitro and cyano groups and alkyl and alkoxy groups each of up to 4 carbon atoms;

wherein X is a direct link or is —O—, —S—, —SO— or —SO$_2$ or has the formula —CR$^3$=CH— wherein R$^3$ is hydrogen or alkyl of up to 4 carbon atoms;

wherein A is straight or branched alkylene or alkenylene of 4 to 8 carbon atoms which may be interrupted by —O—, —S— or —NH—;

and wherein NR$^1$R$^2$ is a cyclic amino group;

provided that when Ar is naphthyl, X is —O— and -A- is —(CH$_2$)$_4$—, —NR$^1$R$^2$ is not morpholino; when Ar is naphthyl or naphthyl substituted by halo, alkoxy or alkyl, X is —O— and A is (CH$_2$)$_{3-8}$, R$^1$R$^2$ of the cyclic amine group does not form an alkylene group;

and when Ar is phenoxazin-10-yl, X is a direct link and A is —(CH$_2$)$_3$— or —(CH$_2$)$_4$—, —NR$^1$R$^2$ is not pyrrolidino, piperidino, morpholino or N-(β-hydroxyethyl)piperazino;

or a pharmaceutically acceptable acid addition salt thereof.

28. A compound according to claim 27 wherein the groups Ar, X, A, R$^1$, R$^2$ and R$^3$ are as defined above.

29. A process for the manufacture of a compound according to claim 27 which comprises the reaction of a compound of the formula:

Ar-X-A-Z wherein Ar, X and A are as defined above and wherein Z is a displaceable group with an amine of the formula HNR$^1$R$^2$, wherein R$^1$ and R$^2$ are as defined above.

* * * * *